United States Patent [19]
Shettigar

[11] Patent Number: 5,876,611
[45] Date of Patent: Mar. 2, 1999

[54] INTRAOPERATIVE BLOOD SALVAGING SYSTEM AND METHOD

[76] Inventor: U. Ramakrishna Shettigar, American Towers #2301, 44 W. 300 South, Salt Lake City, Utah 84101

[21] Appl. No.: 876,557

[22] Filed: Jun. 16, 1997

Related U.S. Application Data

[60] Provisional application No. 60/033,998 Jan. 3, 1997.

[51] Int. Cl.⁶ .......................... B01D 61/00; B01D 61/18; A61M 1/00; A61M 1/34
[52] U.S. Cl. .............................. 210/739; 210/85; 210/86; 210/90; 210/97; 210/103; 210/104; 210/108; 210/111; 210/142; 210/143; 210/195.2; 210/650; 210/741; 210/744; 210/798; 210/805; 604/4; 604/5; 604/6; 604/65; 604/67
[58] Field of Search ..................................... 210/650, 651, 210/739, 741, 744, 746, 767, 797, 798, 805, 806, 85, 86, 90, 97, 103, 104, 106, 108, 109, 111, 195.2, 142, 143, 252, 257.1, 258, 44; 604/4, 5, 6, 65, 67

[56] References Cited

U.S. PATENT DOCUMENTS

| | | |
|---|---|---|
| 2,804,075 | 8/1957 | Borden . |
| 3,896,733 | 7/1975 | Rosenberg . |
| 3,965,896 | 6/1976 | Swank . |
| 3,993,067 | 11/1976 | Schachet et al. . |
| 4,006,745 | 2/1977 | Sorenson et al. . |
| 4,014,329 | 3/1977 | Welch et al. . |
| 4,033,345 | 7/1977 | Sorenson et al. . |
| 4,047,526 | 9/1977 | Reynolds et al. . |
| 4,631,050 | 12/1986 | Reed et al. . |
| 4,744,785 | 5/1988 | Rosenthal et al. . |
| 4,772,256 | 9/1988 | Lane et al. . |
| 4,796,644 | 1/1989 | Polaschegg . |
| 4,798,578 | 1/1989 | Ranford . |
| 4,867,738 | 9/1989 | Mintz . |
| 4,874,359 | 10/1989 | White et al. . |
| 4,886,487 | 12/1989 | Solem et al. . |
| 4,898,572 | 2/1990 | Surugue nee Lasnier et al. . |
| 4,919,817 | 4/1990 | Schoendorfer et al. ................ 210/651 |
| 4,976,682 | 12/1990 | Lane et al. . |
| 5,055,198 | 10/1991 | Shettigar . |
| 5,215,519 | 6/1993 | Shettigar . |
| 5,242,384 | 9/1993 | Robinson et al. . |
| 5,298,171 | 3/1994 | Biesel ........................................ 210/87 |
| 5,378,227 | 1/1995 | O'Riordan et al. .......................... 604/4 |
| 5,385,539 | 1/1995 | Maynard ..................... 604/4 |
| 5,407,425 | 4/1995 | Werner et al. . |
| 5,417,649 | 5/1995 | Kawahara et al. .......................... 604/4 |
| 5,417,650 | 5/1995 | Gordon ....................................... 604/4 |
| 5,423,738 | 6/1995 | Robinson et al. .......................... 604/4 |
| 5,554,293 | 9/1996 | Uhoch . |

Primary Examiner—John Kim
Attorney, Agent, or Firm—Trask, Britt & Rossa

[57] ABSTRACT

An apparatus is disclosed for salvaging a patient's own blood during intraoperative surgical procedures and reinfusing the blood, washed and filtered, to the patient substantially continuously, on-line and in real-time. The apparatus comprises suction means, admixing means for admixing aspirated blood with a washing fluid, filtering means for filtering the admixture through an emboli filter, monitoring means for measuring the amount of cellular component volume in the aspirated, filtered blood, filtration means for removing excess fluid and impurities from the blood, and reinfusion means for introducing the washed and filtered blood to the patient free of emboli. The apparatus is structured to introduce washing fluid to the aspirated blood in proportion to the measured hematocrit level of the blood that is aspirated. Methods are disclosed for priming of the system, cleaning and flushing the apparatus of blood clots and debris by means of reverse filtration and filtration of blood for reinfusion. Methods for automated control of the blood salvaging system and operation are also disclosed.

29 Claims, 8 Drawing Sheets

INTRAOPERATIVE BLOOD SALVAGING SYSTEM AND METHOD

BACKGROUND

This application claims the benefit of Provisional Ser. No. 60/033,998, filed Jan. 3, 1990.

Field of the Invention

The present invention relates to methods and apparatus for recovery, purification and reinfusion of blood lost at a wound site during surgery. More specifically, the present invention relates to aspiration of shed blood from a wound site during intraoperative surgery, on-line purification of aspirated blood by filtration and cell-washing using filtration membranes, and reinfusion of purified autologous blood to the patient on a real-time basis.

Statement of the Art

Significant blood loss from a person may occur during a traumatic injury, during a serious and traumatic surgery, such as open heart surgery, or during post-surgical recovery periods due to hemorrhagic conditions. Significant loss in blood will result in decreased blood pressure, decreased cardiac output and decreased oxygen delivery to tissues, particularly brain cells. For those reasons, the loss of blood should be compensated by blood transfusions as soon as possible.

During an intraoperative period, a pool of shed blood accumulates in the wound site, which obstructs the surgery site unless aspirated from the site. The total loss of blood may vary from 1,000 ml to 15,000 ml depending on the extent and traumatic conditions of surgery. Blood lost during intraoperative or post-surgical recovery periods can be collected in a container and reinfused to the patient provided the salvaged blood is free of impurities. Typical impurities are blood clots, tissue debris, hair, foreign particles, activated coagulation factors, denatured proteins, plasma-free hemoglobin, and any other fluids (e.g., irrigation fluid) that are being added into the wound site by medical personnel.

Usually, suction is provided to remove the shed blood, other accumulated fluids, blood clots and tissue debris. Impurities in the salvaged blood are generally filtered using a 40 micron filter to remove particles greater than 40 microns in size. The blood is then subjected to "cell-washing". The cell washing technique may involve mixing blood with a physiological solution (e.g., saline or Ringer's Solution) in equal proportion to the blood, and then centrifuging the diluted blood to recover the heavier blood cells, which are suitable for reinfusion to the patient. However, the lighter portion of centrifuged fluid (i.e., the top portion in the centrifuge tube) containing platelets, white cells, plasma proteins and antibodies is usually discarded as waste. This represents a significant loss to the patient, particularly the loss of coagulation factors, platelets, white cells and antibodies. Therefore, the efficiency of recovery of blood products by conventional cell washing techniques is low. Additionally, conventional blood recovery methods are not accomplished on-line, in real-time. Rather, they are batch processes involving operator intervention and are subject to human errors and time delay.

Thus it will be appreciated that purification of salvaged blood based on cell-centrifuge machines is not designed to work on a real-time basis. That is, there is considerable lag time (more than 15 minutes) between the moment of aspiration of shed blood and reinfusion of processed autologous blood (i.e., the patient's own blood). This is a significant problem, especially when the patient bleeds rapidly and lost blood volume needs to be compensated immediately. Furthermore, during cell washing by the conventional centrifuge technique, a significant amount of red blood cells is lost, as well as almost all of the white blood cells, platelets and plasma proteins, including antibodies.

Due to the above-identified problems in conventional cell washing techniques, a patient is usually given homologous (donor) blood transfusions rather than his/her own blood, which is still being processed. Problems with homologous blood transfusion are many. The major problem is finding a compatible donor blood which is free of agents which cause side effects, such as anaphylactic reactions, and which does not transmit donor-carried infectious organisms or viruses which cause diseases such as hepatitis, malaria or acquired immune deficiency syndrome (AIDS). At times, it is difficult to find the necessary blood needed for transfusions, and it can be very expensive. As a result, "autotransfusion" (reuse of a patient's own blood) has been receiving significant attention.

There are many existing autotransfusion systems which vary in design and operation. Basically, each is composed of three units—namely, an aspirator unit, a cell washing unit and a blood reinfusion unit. The typical aspirator unit consists of a suction handle attached to suction tubing, which is connected to an emboli filter reservoir. The emboli filter is generally provided with an air vent line, a degassifier, a 40 micron filter and a blood reservoir. Controlled suction is usually applied with a vacuum source via the vent line of the emboli filter. The vacuum aspirates shed blood, along with other impurities, from the wound site into the filter reservoir. Impurities larger than 40 micron size will be trapped in the emboli filter.

Filtered blood is usually pumped to a cell centrifuge machine where it is mixed with an appropriate "washing fluid" and centrifuged for a specified time until the heavier blood cells are separated from the plasma. This method is cumbersome, time consuming and requires an operator to attend the system continuously. Furthermore, there is a loss of precious plasma proteins, antibodies, and white cells, which are required for the body's ability to fight infection. Thus, it would be an advancement in the art to provide an on-line apparatus for providing continuous processing of autologous blood, which would minimize loss of precious blood elements and which would reinfuse to the patient his/her own blood on a real-time basis. It would be a further advancement to provide an automatic system which would reinfuse whole blood at a specified hematocrit level free of air emboli.

SUMMARY OF THE INVENTION

In accordance with the present invention, an intraoperative blood salvaging and purification system removes blood from a wound or surgical site, filters and purifies the blood by the addition thereto of washing fluid at a rate determined by a selected hematocrit level detected in the blood, and returns the blood to the patient on a substantially continuous basis. The intraoperative blood salvaging and purification system is structured to process large amounts of blood and to return the salvaged blood to the patient free of impurities larger than a selected molecular size, and free of emboli. The filtration system of the present invention maintains filtration integrity by providing reverse filtration to flush out clogging impurities from the filtration membrane.

The intraoperative blood salvaging system generally comprises a means for removing blood from a wound site or from an operative or post-operative site and means for mixing the blood with a washing fluid prior to delivering the blood to an emboli filter for initial washing of the blood. The system also includes means for further filtering the salvaged blood to remove impurities larger than a selected molecular size through use of a membrane filter having a selected maximum pore size. The blood salvaging system further includes structural means for delivering filtered and purified blood back to the patient on a substantially continuous basis, free of emboli.

In the present invention, a cardiotomy filter and reservoir are positioned to receive aspirated blood from the wound site and serve to (i) de-aerate the aspirated blood under vacuum; (ii) remove particle emboli, blood clots and other matter larger than a selected micron size; (iii) provide a reservoir large enough to accommodate large volumes of aspirated blood and washing fluid, and maintain a continuous source of liquid for the membrane filter and reinfusion line, thereby eliminating air from entering the membrane filter and reinfusion line; and (iv) monitor the extent of dilution of the aspirated blood (i.e., washing/blood ratio) by the washing fluid. To meet those requirements, the cardiotomy reservoir is provided with (i) an emboli filter having about a 40 micron pore size; (ii) a reservoir having a capacity of about 4 to 5 liters; (iii) a hematocrit sensor (also referred to hereafter as "HCT-1") positioned at the lower end of the reservoir at a point thereof corresponding to a capacity of about 50 ml to 200 ml; (iv) a liquid overflow sensor which detects when liquid reaches the top end of the reservoir and generates an alarm signal if an overflow condition is imminent; and (v) a liquid level sensor positioned in connection with the reservoir in a location corresponding to a reservoir capacity of about 50 ml to 200 ml. The hematocrit sensor, HCT-1, may preferably serve as the most reliable liquid level sensor. While ultrasonic level sensors have been used in the past as level sensors, they may occasionally fail due to air entrapment between the sensor and the reservoir wall.

The cardiotomy filter is usually operated under a maximum vacuum pressure of −120 mm Hg to remove or aspirate blood from the wound site. Aspirated blood must be mixed with a washing fluid in order to remove impurities present in the blood. The efficiency of removal of impurities is proportional to the volume of washing fluid used for cell washing. In conventional methods, blood and washing fluid are mixed in equal proportion. While bleeding in the wound site varies with time, ranging from 0 to 3,000 ml/min., the actual bleeding rate at any given moment is not known. Thus, it is difficult to provide a continuous proportionating device which would regulate the flow rate of washing fluid in proportion to the bleeding rate, which is an unknown variable. Such proportioning has been attempted, however, in prior devices by measuring the bleeding rate in the suction tubing or suction handle using some sophisticated sensors such as ultrasonic, thermal, optical, laser or electronic sensors and microprocessor-based control units.

The present invention presents a novel method of providing the optimal amount of washing fluid proportional to the amount of blood being aspirated by measuring the hematocrit (HCT-1) of the aspirated blood, pre-mixed with washing fluid, which is collected in the cardiotomy reservoir. The hematocrit value of a given sample of blood corresponds to the amount of blood cellular debris contained in the blood. If the measured hematocrit value is less than a selected pre-set value (for example, HCT-1=11.7%), no washing fluid is delivered for mixture with the aspirated blood. If the measured hematocrit value is greater than the pre-set value, then washing fluid is delivered at a pre-set maximum flow rate for mixture with aspirated blood until the measured hematocrit value (HCT-1) decreases below the preset value. Washing fluid delivery stops irrespective of the measured hematocrit value HCT-1 when there is a detected overflow in the cardiotomy reservoir as monitored by an overflow level sensor.

The present invention provides a continuous on-line method of removing impurities from blood which are greater than a specified molecular size and reinfusing the purified blood to the patient at a specified hematocrit value, free of air emboli. This is achieved by pumping the filtered blood from the emboli filter reservoir through a membrane ultrafilter or a plasma filter under a positive pressure while the fluid portion (i.e., a percentage of the non-cellular volume) of the filtered blood is continuously measured using a second on-line hematocrit monitor (HCT-2) located at the blood outlet of the membrane filter. An ultrafilter may be used for membrane filtration and may preferably have a pore size ranging from 40,000 daltons to 400,000 daltons molecular weight cut off. It may be most suitable to use a membrane with a pore size cut off of 100,000 daltons. However, if larger size impurities are to be removed, then a pore size of 400,000 daltons or even a plasma filter having a pore size of 0.4 micron may be used.

Suitable membrane filters, such as ultrafilters or plasma filters, are structured with a blood side (i.e., comprising one or more pathways for blood movement) and a filtrate side (i.e., comprising a fluid waste product pathway). The blood side and filtrate side are separated by one or more porous membranes having a selected porosity as previously described. A blood exit port is in fluid communication with the blood side to direct filtered and purified blood from the membrane filter for reinfusion. A filtrate outlet is in fluid communication with the filtrate side of the membrane filter to remove and dispose of the filtrate.

The membrane filtration rate (i.e., the rate at which waste fluid is removed from the blood) is regulated by a filtrate pump, the speed of which is set to provide a flow rate which is inversely proportional to the measured hematocrit HCT-2. The maximum speed of the filtrate pump corresponds to the maximum permissible filtration rate (for example, filtration rate =332 ml/min corresponding to a maximum blood processing rate of 166 ml/min). The maximum speed at which the filtrate pump may operate is dictated by the operating characteristics or specifications of the membrane filter. If the measured hematocrit HCT-2 is greater than a predetermined set point (for example, the hematocrit of the processed blood to be infused to the patient is 30%), then the filtrate pump speed is gradually decreased until the HCT-2 value approaches or equals the set point.

In the present invention, the fraction of cellular volume, or hematocrit, in the blood being processed through the apparatus is monitored continuously by measuring the impedance of the blood at a specified frequency using two stainless steel electrodes positioned near the outlet of the membrane filter or plasma filter. The electrodes supply a current of ten micro amperes at a frequency of five thousand Hertz. Measured conductivity of blood is known to be proportional to the fraction of noncellular fluid volume in the blood.

In the present invention, filtered blood is not continuously recirculated to the emboli filter during membrane filtration as is the case in prior devices. Rather, the filtered blood, during membrane filtration, is continuously directed from the membrane filter to a blood collection bag for reinfusion to the patient in a single pass. During membrane filtration, negative pressure exists on the filtrate side of the membrane filter. Occasionally, the negative pressure on the filtrate side, as measured by a negative pressure sensor connected thereto, may decrease below a permissible level (e.g., −50 mm Hg, as determined by the specifications of the membrane filter) due to the gradual deposition of protein and cellular particles on the blood side of the membrane filter. Such deposits cause a significant decrease in the membrane filtration rate. When the negative pressure decreases below the determined level, filtration of blood is stopped and reverse filtration is conducted for a selected time period (e.g., one minute).

During reverse filtration, washing fluid from a washing fluid bag is pumped through the filtrate side of the membrane filter, causing reverse filtration across the membrane. Reverse filtration clears the solid deposits from the membrane pores and the resulting fluid is reintroduced to the cardiotomy filter via the suction line so as to remove any particulates, blood clots and air emboli from the reverse-filtered fluid. The reverse-filtered fluid is collected in the cardiotomy reservoir to be purified further by the membrane filter in the next cycle of membrane filtration. In the present invention, reverse filtration using washing fluid is continued for the pre-set period (for example, 1 minute), and then membrane filtration of the diluted blood is resumed.

During membrane filtration, high positive pressure may occur on the blood side of the membrane filter as indicated by a pressure sensor connected thereto. This high pressure (e.g., 150 mm Hg) may be due to (i) excessively high blood flow rate, (ii) excessively high hematocrit, (iii) clogging or clotting in the blood lumen of the membrane filter, or (iv) blockage in the blood reinfusion line. High pressure is relieved respectively by (i) decreasing the blood pump speed, (ii) decreasing the filtrate pump speed, (iii) reverse filtration of the membrane filter using the washing fluid, (iv) checking for any blockage in the blood infusion line, and/or (v) heparinization of blood and washing fluid.

A single tube clamp with four operative channels is provided to accommodate at least four tubes of the apparatus. The single clamp operates to selectively open certain tubings or fluid lines while occluding others to effect a switch from membrane filtration to reverse filtration automatically. When the single clamp is not activated, membrane filtration occurs by allowing the purified blood to flow into a blood collection bag, by allowing the washing fluid to flow directly into the suction line of the cardiotomy filter reservoir and by regulating the filtrate pump speed. When the single clamp is activated for initiating reverse filtration, both the blood and filtrate pumps stop, the washing fluid is directed to the filtrate port of the membrane filter instead of to the suction line, and the blood outlet line of the membrane filter is directed to the suction line of the cardiotomy filter reservoir instead of to the blood collection bag. As reverse filtration proceeds, the washing fluid flushes out the contents of the blood side of the membrane filter by flowing across the membrane from the filtrate side to the blood side, and then it flows into the cardiotomy reservoir after being filtered by the cardiotomy emboli filter. A rise in the liquid level in the cardiotomy reservoir results. At that time, the HCT-1 sensor detects liquid (not air) which signals reverse filtration to stop and membrane filtration to start. In the present invention, the reliability and simplicity of the system is improved by the use of the single clamp instead of two or four clamps to switch from membrane filtration to reverse filtration.

During membrane filtration, the purified (washed) blood leaving the blood exit port of the membrane filter flows into a blood collection bag, which is hung from an i.v. pole. The height of the blood collection bag above the membrane filter, and the speed of the blood pump, determine the positive pressure required for membrane filtration. The height of the blood collection bag may be adjusted such that the positive pressure (as indicated by a pressure sensor located at the inlet port of the membrane filter) does not exceed a maximum permissible pressure (for example, 150 mm Hg).

A programmable control unit is connected to the blood salvaging system of the present invention and is in electrical communication with many elements of the system, including all of the hematocrit sensors, the overflow sensor, all of the pressure sensors, all of the pumps, the multi-channel clamp and a clamp associated with the blood reinfusion line. The control unit is programmed to emit an alarm responsive to certain perceived conditions, such as a dangerous increase in pressure, so that an operator of the system (i.e., surgical personnel) can monitor the operation of the system as may be necessary. The control unit includes programming which determines, for example, when the pumps and clamps should be activated or deactivated responsive to a given condition detected by the various sensors. The present invention is structured to provide a most reliable and efficient intraoperative autotransfusion system which can operate on-line continuously on a real-time basis in order to collect, purify and reinfuse to a patient his/her own shed blood.

BRIEF DESCRIPTION OF THE DRAWINGS

In the drawings, which illustrate what is currently considered to be the best mode for carrying out the invention.

DETAILED DESCRIPTION OF THE DRAWINGS

The structural elements of the blood salvaging apparatus of the present invention are shown in FIGS. 1A, 1B, 7 and 8. A programmable control unit is associated with the structural elements of the apparatus. The control unit, designated CU in the drawings, is in electrical communication with several of the structural elements of the apparatus to monitor and regulate the operation of the apparatus as a whole, as explained more fully hereinafter. However, such electrical connections are not shown in the drawings for the sake of clarity. Some of the programmed functions provided by the control unit CU are also illustrated in FIGS. 2–6. At initiation of a blood salvaging episode, the control unit CU is turned on and all timing clocks and alarms are set at zero or are reset. At that time, certain values and times, the nature of which are described more fully hereinafter, may be set at a default value or time. Alternatively, some of the values or times may be input by the operator, including, for example, a washing fluid/blood dilution ratio, the length of time for conducting reverse filtration and the speed of the blood pump to coordinate with the anticipated length of the surgical procedure.

Figure 1A:
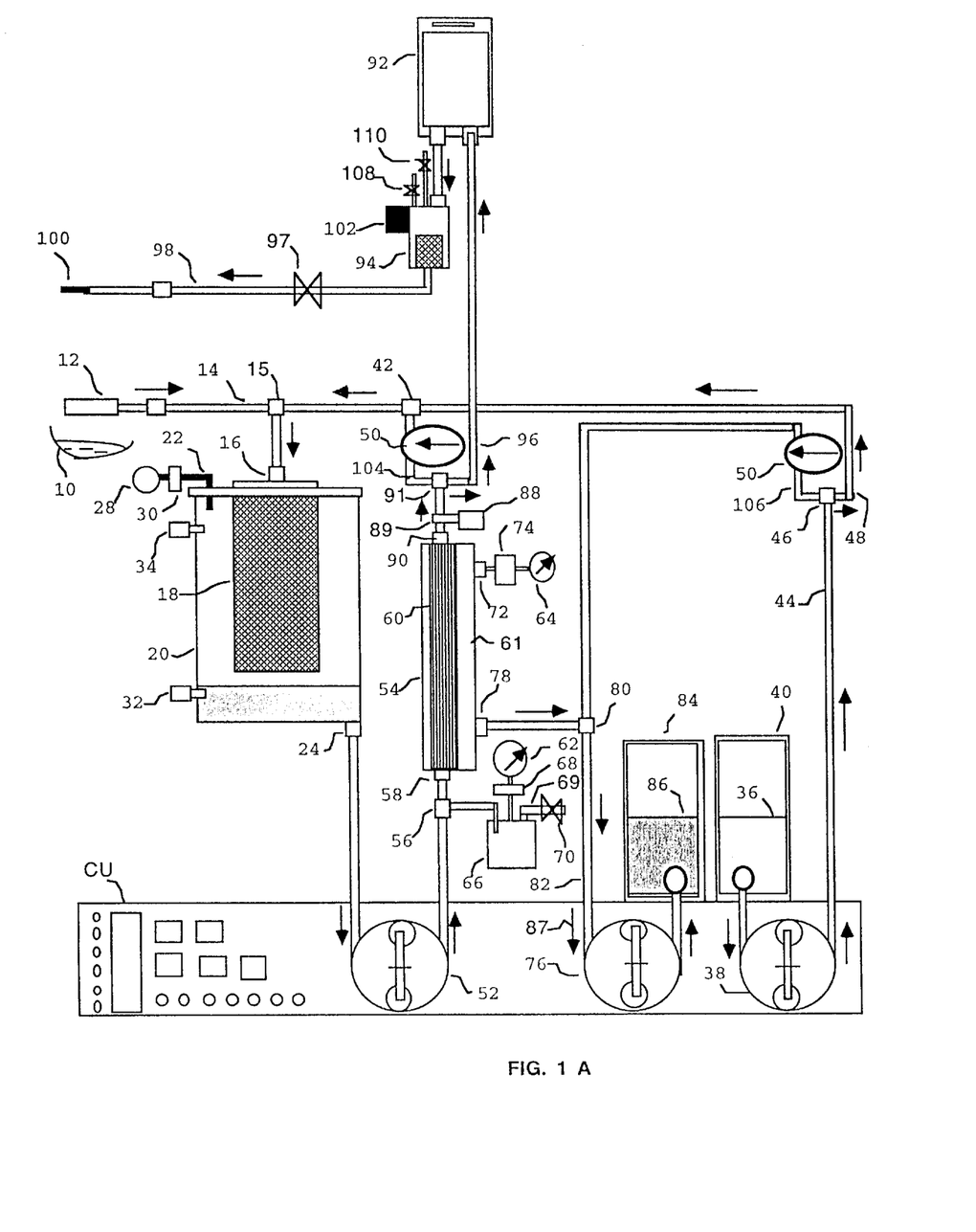
FIG. 1A is a schematic diagram illustrating the intraoperative autotransfusion system of the present invention operating in the membrane filtration mode.

Referring to FIG. 1A, the location of a wound site is designated at 10. When there is bleeding in the wound site 10, shed blood is aspirated from the site by suction means 12. The suction means 12 generally includes a conventional handle and a suction tip (not shown in detail). The suction means 12 is connected to a length of suction tubing 14, the other end of which is connected to the blood inlet port 16 of an emboli filter 18, otherwise called a cardiotomy filter, via a Y-connector 15. The emboli filter 18 may generally consist of a polyurethane sponge coated with an antifoam silicone compound which assists in the degassification of the aspirated blood. The polyurethane sponge may be enclosed by a filter fabric having a pore size of about 40 microns to assure removal from the blood of particles larger than 40 microns in size. The emboli filter 18 is enclosed in a structural casing which provides a large reservoir 20. The reservoir 20 is provided with a vent line 22 at its top end and a blood outlet port 24 at its bottom end. The vent line 22 is connected to a vacuum line which may be connected to a controlled vacuum source 28 via an air filter 30. Most operating rooms are generally equipped with a vacuum source which can be controlled at any desired value.

In accordance with the present invention, washing fluid is mixed with the aspirated blood at a rate proportional to the detected hematocrit of the blood collected in the reservoir 20. Thus, a hematocrit sensor 32 (HCT-1) is connected to the wall of the reservoir 20 at a level thereof corresponding to about a 100 ml to 200 ml capacity of the reservoir 20. A minimum volume of liquid (100 ml to 200 ml) must always be maintained in the reservoir 20 as a liquid seal to prevent air from being drawn into the system. In this embodiment, the HCT-1 hematocrit sensor 32 monitors both the air-liquid interface and the hematocrit of the liquid. Alternatively, both a hematocrit sensor and a separate sensor for detecting the air-liquid interface may be used. An overflow sensor 34, which may preferably comprise another hematocrit sensor, is connected to the wall of the reservoir 20 at a level thereof corresponding to about a 4 to 5 liter capacity of the reservoir 20. The overflow sensor 34 detects the liquid/air interface of the fluid in the reservoir 20 at that level and initiates an alarm if liquid overflow in the reservoir 20 is imminent.

Figure 8:
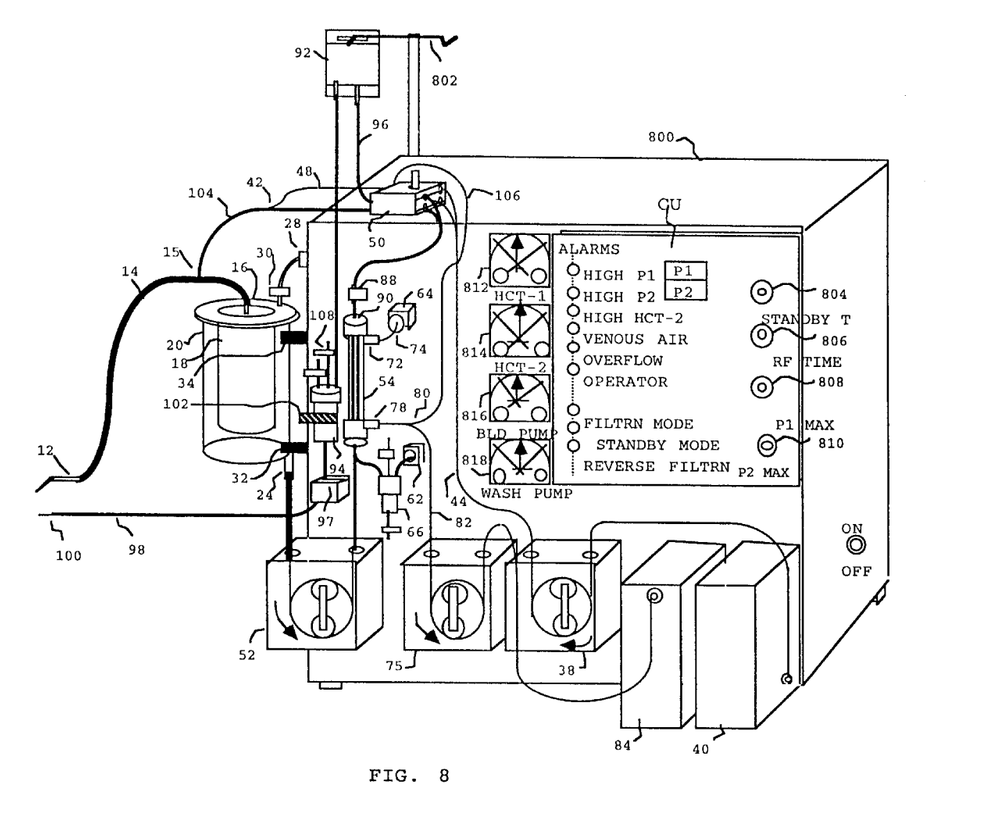
FIG. 8 is a perspective view of a representational model of the control unit connected to the structural elements of the blood salvaging apparatus.

A pre-set value is determined for detecting by the HCT-1 sensor 32, and that value is stored in the control unit (FIG. 8). The pre-set value of HCT-1 is dependent on the washing fluid/blood dilution ratio and on an assumed hematocrit level of the blood as it is shed from the wound or surgical site. Thus, for example, assuming that the hematocrit level of the shed blood at the wound site is 30%, and further assuming a desired washing fluid/blood dilution ratio of two (which is a preferred ratio), the resulting hematocrit value that should be detected by the HCT-1 sensor 32 is 11.7%. If, for example, the washing fluid/blood dilution ratio is set by the operator to be 1.5, then the pre-set hematocrit value would be higher than 11.7%.

When the hematocrit measured by the HCT-1 sensor 32 is greater than a preset value (e.g., 11.7%), then washing fluid 36 is pumped rapidly (e.g., 332 ml/min) by a washing fluid pump 38 towards the suction line 14 from a retainer bag 40. The washing fluid travels through a washing fluid conduit 44 connected to a Y-connector 46 and through a first washing fluid conduit 48 which is engaged by a tubing clamp 50. The washing fluid 36, which may preferably contain heparin, is mixed with aspirated blood at the Y-connector 15 and the admixture flows into the emboli filter 18 where it collects in the reservoir 20. The washing fluid pump 38 remains on until the hematocrit detected by the HCT-1 sensor 32 falls below the pre-set value (e.g., less than 11.7%).

When the diluted blood volume in the reservoir 20 is above the minimum volume of 100 ml to 200 ml, as detected by the hematocrit HCT-1 sensor 32, then the blood pump 52 operates to draw diluted blood from the reservoir 20. The diluted blood moves through the blood outlet port 24, to the membrane filter 54 via a Y-connector 56 and through the blood inlet port 58 of the membrane filter 54. The membrane filter 54 may be a conventional membrane separator with a pore size ranging from 40,000 daltons to 400,000 daltons molecular weight cut off. It may be preferable to use a membrane with a pore size cut off of 100,000 daltons. However, if larger size impurities are to be removed, then a pore size of 400,000 daltons, or even a plasma filter having a pore size of 0.4 micron may be used. The membrane filter is generally structured with a blood pathway (or several blood pathways, such as a plurality of tubules) and a filtrate pathway. The blood and filtrate pathways are separated by one or more membranes of selected porosity as described above. As blood passes through the membrane from the blood side 60 of the membrane filter 54 to the filtrate side 61, fluid and other components below the size of the membrane pores are removed as filtrate and move to the filtrate side 61 of the membrane filter 54 to eventually exit through the filtrate outlet 78.

Filtration is induced by a controlled transmembrane pressure differential which is monitored by two pressure sensors 62 and 64. Positive pressure, P1, at the blood inlet port 58 is measured by a positive pressure sensor 62 which is connected to the Y-connecter 56 via an air pressure chamber 66 and an air filter 68. The air chamber 66 and air filter 68 are required to maintain sterility in the blood lines and also to keep the blood from contacting the pressure sensor 62, thereby enabling the sensor to function reliably. A vent line 69 with a tubing clamp 70 is connected to the air pressure chamber 66 to provide pressure relief if necessary. An audible alarm device, such as may be located in the control unit (FIG. 8), may be interconnected with the pressure sensor 62 to sound an alarm during high pressure conditions. Negative pressure, P2, on the filtrate side 61 of the membrane filter 54 is measured by a negative pressure sensor 64 which is connected to the filtrate side port 72 via an air filter 74. Negative pressure P2 on the filtrate side 61 is induced by the filtrate pump 76, which draws filtrate from the membrane filter 54 through the filtrate outlet 78 via a Y-connector 80 and a filtrate line 82. The filtrate pump 76 pumps the filtrate 86, in the direction of arrows 87, into a collapsible waste bag 84 where the filtrate (waste) 86 is collected.

The speed of the filtrate pump 76 is regulated by a third hematocrit sensor 88 (HCT-2) located near the blood exit port 90 of the membrane filter 54. When the hematocrit detected by the HCT-2 sensor 88 is less than a pre-set value (e.g., 30%), the filtrate pump 76 speed increases to maximize filtration and reaches a maximum permissible value (e.g., 332 ml/min), as determined by the manufacturer's specifications for the pump and the membrane filter. The pre-set value for the HCT-2 sensor 88 is that hematocrit value of the blood which is most appropriate for the patient. In other words, it is generally considered that a 30% hematocrit level is appropriate for reinfused blood, but the hematocrit level of the blood may normally range from 20% to 40%. The HCT-2 sensor 88 may be set (FIG. 8) to detect any hematocrit value in that range. The maximum permissible filtration rate is determined by the manufacturer's specifications for the membrane filter (e.g., in terms of the pressure values that may be maintained in the membrane filter).

At the commencement of membrane filtration, the blood pump 52 is off, but the speed of the blood pump 52 is increased gradually over time until it reaches a selected maximum speed, for example, 500 ml/min. The maximum speed is determined by the manufacturer's specifications for the pump and by the selected dilution ratio of washing fluid to blood. The blood pump 52 speed is set by the control unit CU (FIG. 8) to equal that of the filtrate pump 76 speed when the measured hematocrit HCT-2 at the blood exit port 90 is zero, as is the case when the apparatus is initially primed for operation by circulating washing fluid through the system. When HCT-2>0, the blood pump 52 speed is programmed to operate at a faster speed than the filtrate pump 76 speed. When HCT-2<0, the filtrate pump remains off. When the HCT-2 value falls below a pre-set value (e.g., 30%), the filtrate pump 76 speed increases such that the measured hematocrit value HCT-2 at the blood exit port 90 becomes almost equal to the pre-set value. By the method just described, the system operates to maintain a substantially even hematocrit level in the reinfused blood.

The hematocrit (cellular volume fraction) of blood is measured continuously by measuring the conductivity of the blood at a specified frequency using two stainless steel electrodes 89 positioned in proximity to the blood exit port 90 of the membrane filter 54. Such conductivity monitors are readily available on the market (Sedatelec, Chemin des Muriers, Irigny, France). The electrodes 89 supply to the blood a current of ten microamperes at a frequency of five thousand Hertz. Measured conductivity of blood is known to be proportional to its noncellular volume fraction.

Figure 1B:
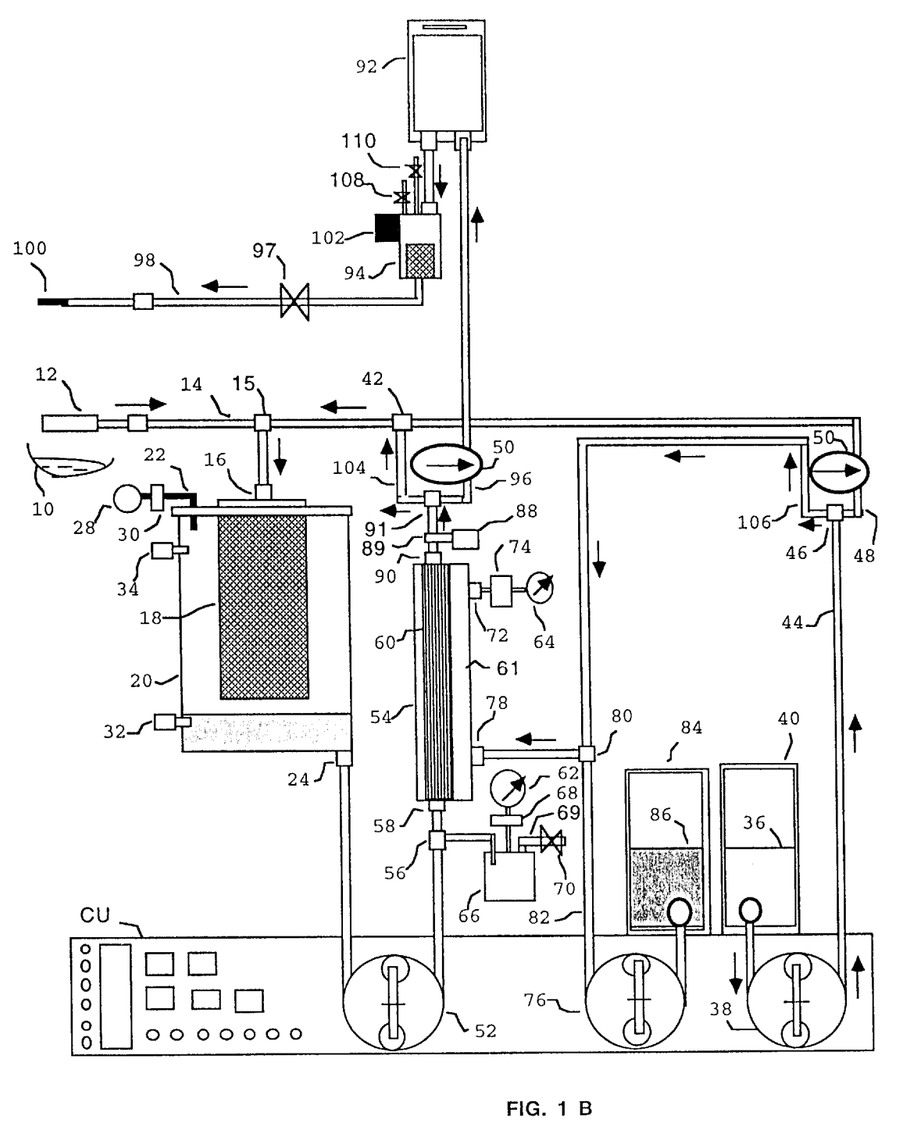
FIG. 1B is a schematic diagram illustrating the intraoperative autotransfusion system shown in FIG. 1A operating in the reverse filtration mode.

The washed blood leaving the blood exit port 90 of the membrane filter 54 flows into a conventional collapsible blood collection bag 92 via a Y-connector 91 and through blood line 96 positioned in the clamp 50. It should be noted that clamp 50 is shown in FIG. 1A and FIG. 1B as if it were two separate clamps for the sake of clarity. However, there is, in fact, only one clamp 50 (see FIG. 8) which is structured to engage and alternatively clamp four different tubing lines, namely washing fluid lines 48 and 106 and blood circulation lines 96 and 104. The structure and operation of the clamp 50 is described more fully hereinafter. It should be noted, however, that during filtration, washing fluid line 48 and blood circulation line 96 are open and washing fluid line 106 and blood line 104 are occluded in a closed position by the clamp 50.

The blood collection bag 92 may be hung from an i.v. pole above the membrane filter 54. The blood collection bag 92 serves as a reservoir for the washed and filtered blood to be reinfused to the patient. It also serves to provide a positive pressure condition for membrane filtration and for blood reinfusion to the patient by virtue of its positioning above the membrane filter and above the level of the patient. Blood flows by gravity from the blood collection bag 92 through a venous filter 94, a venous valve 97, a venous reinfusion line 98 and a venous catheter 100 which is inserted in the patient. The venous filter 94 removes any blood clots from the blood prior to its reinfusion and also serves to trap any air emboli. An ultrasonic air detector 102 mounted to the venous filter 94 detects entrapment of any air emboli in the venous filter 94.

The venous valve 97 is structured to remain in a closed position when no power is applied to the system. That is, it requires the application of electricity to keep the venous valve 97 open so that blood may be reinfused to the patient. In the event of a power failure, however, the venous valve 97 will automatically close, preventing reinfusion. Further, the venous valve 97 will remain open as long as no air emboli are detected in the venous filter 94 as monitored by an ultrasonic air detector 102. When the air detector 102 detects air emboli, the venous valve 97 closes and activates an audio/visual alarm (e.g., "Air in the Venous Line"). Once the alarm is activated, it may be cancelled only by the operator, and the venous valve 97 may be reopened only after venting out any trapped air via the vent line 108 attached to the venous filter 94.

In the present invention, the blood salvaging system automatically switches from membrane filtration (i.e., blood washing) to reverse filtration whenever one of three conditions occur, as described below:

(i) When the liquid level in the reservoir 20 falls below the pre-set limit of 100 ml to 200 ml as monitored by the HCT-1 sensor 32, the system immediately defaults to a standby mode and the blood pump 52, filtrate pump 76 and washing fluid pump 38 stop for a selected period (i.e., one minute). During the period of standby mode, if the liquid level in the reservoir 20 rises above the pre-set limit, then the standby mode is cancelled and the system returns to the membrane filtration mode. However, if during the standby period the liquid level continues to remain below the pre-set limit, then at the end of the standby period, the system switches automatically to reverse filtration.

(ii) When the positive pressure sensor 62 continuously detects a high pressure condition in the blood line at the Y-connector 56, despite a decrease in the speed of the blood pump 52, then the system switches to reverse filtration for a one minute period. That is, when the high pressure alarm (FIG. 8) is activated, the blood pump 52 is gradually decreased from a maximum speed (e.g., 500 ml/min) to a selected fraction of the maximum speed (e.g., 50% of 500 m./min.). However, if the high pressure alarm persists despite the decrease in the blood pump 52 speed below the selected fraction of the maximum speed, the system switches to reverse filtration for one minute.

(iii) When the negative pressure sensor 64 detects a high negative pressure condition on the filtrate side 61 of the membrane filter 54, as may be indicated by the activation of an audible alarm (FIG. 8) associated with the pressure sensor 64, then the system switches to reverse filtration for one minute.

In the present invention, reverse filtration is initiated and controlled by the activation of a single clamp 50, which has four tubing channels to accommodate tubing lines 96, 104, 48 and 106. The first two channels of the single clamp 50 retain blood lines 96 and 104 which both connect to the Y-connector 91 in fluid communication with the hematocrit HCT-2 sensor 88 located in proximity to the blood exit port 90 of the membrane filter 54. When the clamp 50 is not activated (i.e., not pneumatically driven), line 104 remains clamped in a closed position and line 96 remains open, as shown in FIG. 1A. The non-activated condition of the clamp 50 is represented by the left-facing arrow of the clamp 50. When the clamp 50 is activated to initiate reverse filtration, the clamp 50 mechanism moves to clamp off line 96 and to open line 104, as shown in FIG. 1B. The other two tubing channels of the clamp 50 retain washing fluid lines 48 and 106, both of which connect to the Y-connector 46 positioned downstream from the washing fluid pump 38. When the clamp 50 is not activated, line 106 is clamped in a closed position and line 48 remains open, as shown in FIG. 1A. When the clamp 50 is activated to initiate reverse filtration, the clamp 50 mechanism moves to occlude line 48 and open line 106, as shown in FIG. 1B. The mechanism of the clamp 50 is disclosed more fully hereafter.

FIG. 1B describes the blood salvaging system of the present invention in the reverse filtration mode. The structural elements shown in FIG. 1B are the same as those in FIG. 1A, except that clamp 50 is activated, as suggested by the right-facing arrow associated with the clamp 50 shown and the blood pump 52 and filtrate pump 76 are off. When reverse filtration is initiated, both the blood pump 52 and the filtrate pump 76 stop, but the washing fluid pump 38 remains on. The clamp 50 moves upon activation to permit the flow of washing fluid 36 from the fluid retainer bag 40 to the filtrate outlet 78 of the membrane filter 54 via washing fluid conduit 44, through the Y-connector 46, through line 106 and through the Y-connector 80 to the filtrate outlet 78. Washing fluid line 48 remains closed. The washing fluid pumped to the filtrate outlet 78 flows through the membrane pores from the filtrate side 61 to the blood side 60 of the membrane filter 54. During this procedure, the membrane pores are cleared of any cellular or particle deposits. The resulting washing fluid, in which is suspended cellular and particle deposits dislodged from the membrane pores, leaves the blood exit port 90 and flows to the inlet port 16 of the emboli filter 18 via the Y-connector 91, blood line 104 and Y-connectors 42 and 15. Blood line 96 remains closed during this time.

Figure 2:
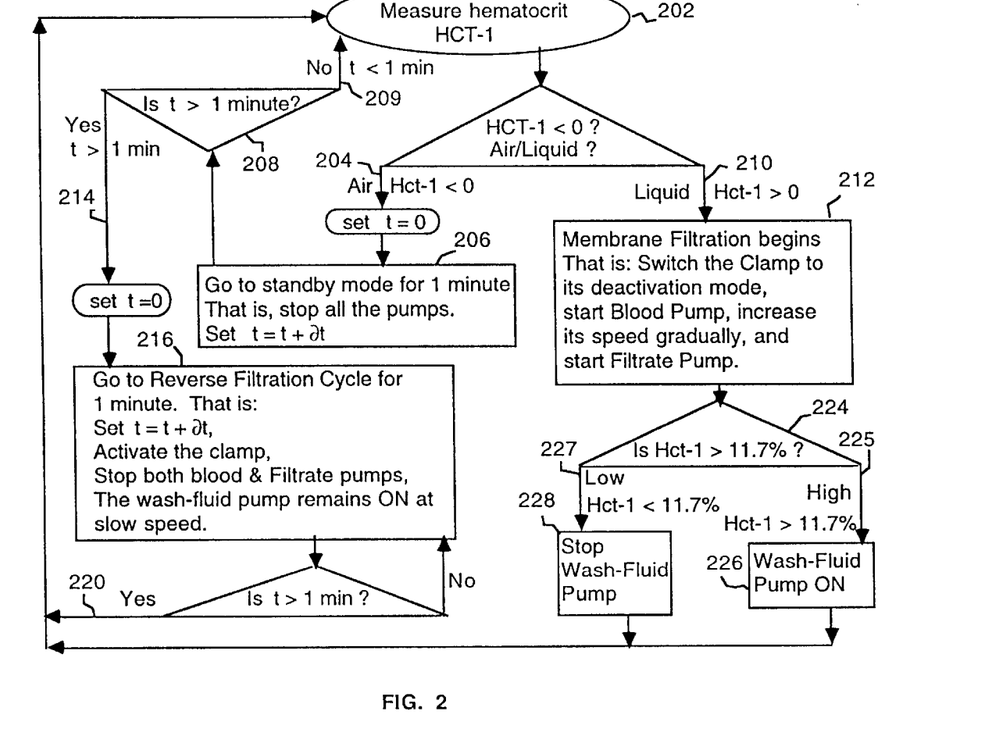
FIG. 2 is a schematic diagram illustrating the function and control logic of the hematocrit sensor (HCT-1) located at the lower end of the cardiotomy reservoir.

The structural elements of the apparatus having been described, FIG. 2 schematically illustrates the control logic defining the interaction between the hematocrit HCT-1 sensor 32, the washing fluid pump 38, blood pump 52, filtrate pump 76 and the clamp 50, all of which are controlled by the control unit (FIG. 8). An amount of washing fluid is circulated through the system to prime the system and to remove any air bubbles. As previously described, the hematocrit HCT-1 sensor 32 monitors 202 both the hematocrit and the liquid-air interface in the reservoir 20. If the measured hematocrit value is less than zero 204, the HCT-1 sensor 32 has detected air instead of liquid; that is, the liquid level in the reservoir 20 is below the pre-set minimum limit. The system automatically switches over to the standby mode 206 for a pre-set time period 208 (e.g., one minute). At the initiation of standby mode, the washing fluid pump 38, blood pump 52 and filtrate pump 76 are stopped 206 and the clock is initialized and set to begin the selected time period "t." A further drop in the level of liquid in the reservoir 20, below the pre-set minimum limit, is prevented by the stoppage of both the blood pump 52 and the filtrate pump 76. The washing fluid pump 38 need not be stopped during the standby mode, but stoppage of the washing fluid pump 38 during standby preserves washing fluid which may otherwise be used for filtration. The period of the standby mode may be pre-set by the operator to any desired length of time at initiation of the system (FIG. 8).

The HCT-1 sensor 32 continues to monitor the liquid/air interface during the standby mode 209. Blood may be aspirated into the reservoir 20 during the standby mode, thereby increasing the level of liquid in the reservoir 20 above the pre-set minimum limit. If the liquid level in the reservoir 20 rises above the pre-set minimum level during the standby period (i.e., HCT-1>0) 210, the standby mode is cancelled and membrane filtration re-commences 212. However, if no blood is aspirated during standby, the level of liquid in the reservoir 20 may remain constant or may drop even further below the minimum limit. If there is no detected increase in the fluid level (i.e., no interruption of the standby mode) at the end of the standby period 214 (i.e., after the one minute period, or t+δt), the system automatically switches to reverse filtration 216 which raises the liquid level above the pre-set minimum level by the introduction of washing fluid and blood from the membrane filter 54 into the reservoir 20. The period of reverse filtration may be pre-set by the operator at the initiation of the system (FIG. 8). In FIG. 2, the pre-set period is shown as one minute.

During reverse filtration 216, the clamp 50 is activated, and both the blood pump 52 and filtrate pump 76 remain off while the washing fluid pump 38 remains on at a low speed. The resulting mixture of washing fluid and blood leaving the blood exit port 90 and entering the emboli filter 18 via line 104 accumulates in the reservoir 20, which leads to a rise in the level of liquid above the minimum limit. At the end of the reverse filtration period 220 (i.e., t+δt), the hematocrit is remeasured 202. The HCT-1 sensor 32 should detect liquid 210. The clamp 50 returns to the inactive mode and membrane filtration begins again 212.

At re-commencement of membrane filtration, or the blood washing period, the speed of the blood pump 52 increases gradually and the filtrate pump 76 is re-started. Contemporaneous with re-commencement of membrane filtration, the hematocrit level of the blood in the reservoir 20 is determined by the HCT-1 sensor 32, at 224. If the hematocrit level is above the pre-set hematocrit value 225, the washing fluid pump 38 is started 226 and will remain on as long as the measured hematocrit HCT-1 remains above the pre-set hematocrit value (e.g., 11.7%) 202. If the HCT-1 value is less than the pre-set limit 227 at commencement of membrane filtration, the washing fluid pump 38 stops or remains off 228, thereby preventing excess dilution of aspirated blood. By the above described control logic, the invention automatically regulates the washing/blood ratio at a desired value and maintains a liquid seal in the reservoir 20 such that a mixture of washing fluid and blood is circulated in the system during the entire period of the surgical procedure irrespective of whether bleeding and aspiration, are occurring at any given time.

Figure 3:
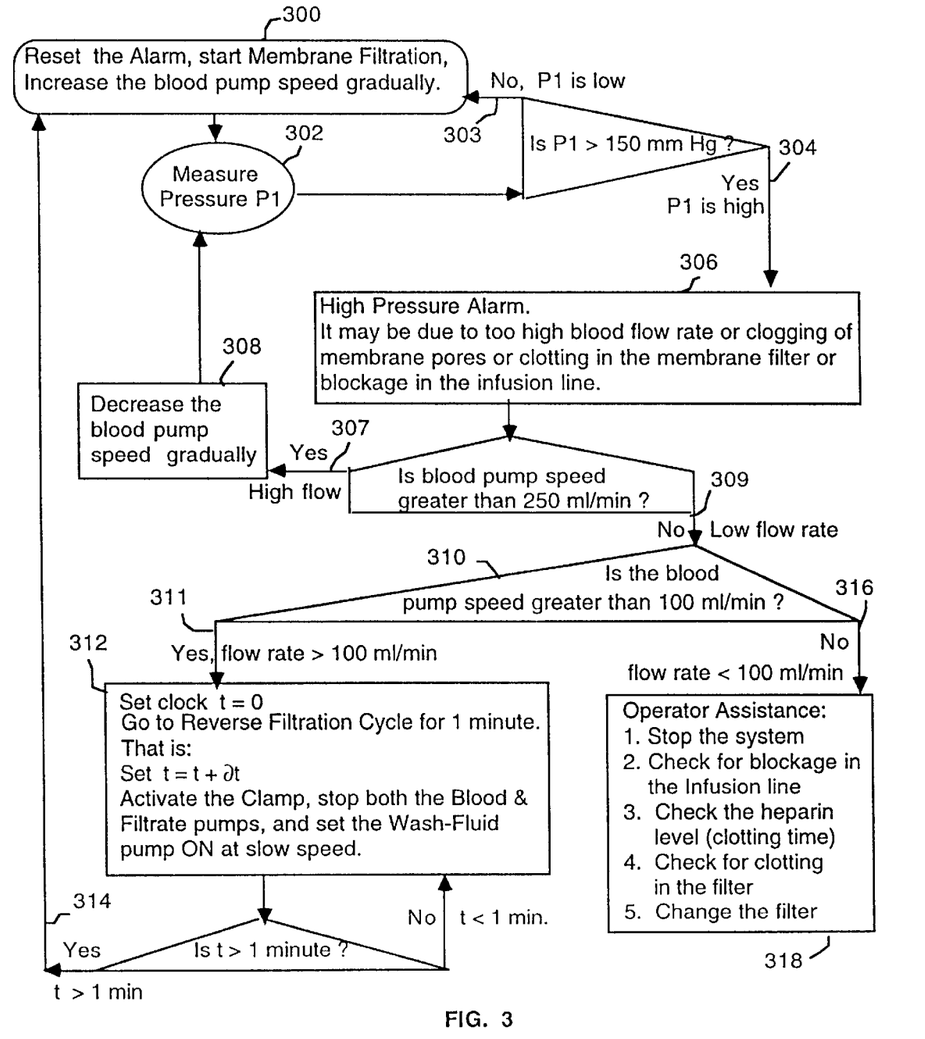
FIG. 3 is a schematic diagram illustrating the function and control logic of the positive pressure sensor (P1) located at the membrane filter blood inlet.

FIG. 3 schematically illustrates the control logic of the pressure sensor 62 and its interactions with the clamp 50, the washing fluid pump 38, the blood pump 52 and the filtrate pump 76. The pressure sensor 62 measures the positive pressure, P1, at the blood inlet port 58 of the membrane filter 54. P1 may rise due to (i) an increase in blood flow rate, (ii) an increase in the hematocrit of circulating blood, (iii) a blockage in the reinfusion line 98, or (iv) a blockage in the blood side 60 of the membrane filter 54 by blood clots, which may be caused by insufficient heparinization. A P1 value greater than a selected maximum pressure may damage the membrane filter 54 and also damage the blood cells travelling through the membrane filter 54, causing hemolysis. The maximum limit of the pressure P1 is specified by the manufacturers of membrane filters. In FIG. 3, an upper limit value for P1 is shown to be 150 mm Hg, reflecting a pressure value above which a dangerously high pressure condition may be reached. Therefore, 150 mm Hg represents a safe upper limit.

At initiation of the blood salvaging system 300, membrane filtration starts and the speed of the blood pump 52 increases gradually from zero. The alarm is also re-set. Measurement of positive pressure begins 302. As long as P1 is not greater than 150 mm Hg 303, the blood pump 52 will gradually increase in speed until the blood pump 52 reaches a selected maximum speed (e.g., 500 ml/min.) It should be noted that at initiation of the apparatus, the surgical personnel may program into the control unit (FIG. 8) the desired maximum speed of the blood pump 52 in accordance with the manufacturer's specifications for the particular membrane filter.

It is preferable to operate the system at as high a blood flow rate (i.e., 500 ml/min.) as possible since blood processing rates (i.e., the rate at which purified blood is reinfused to the patient) increase with the increase in blood flow rate. However, as membrane filtration continues over a prolonged period, increased amounts of protein and blood cell adhesion occur on the blood side 60 of the membrane filter 54, which may partially clog the membrane and lead to higher P1 values, despite a reduction in blood flow rate to as low as 250 ml/min. (i.e., corresponding to 50% of the maximum blood flow rate). When the blood pump speed is decreased, however, the blood processing rate, or the rate at which the purified blood is reinfused to the patient, also decreases. Therefore, the system should operate as close to the maximum blood pump speed as possible while staying within a safe P1 value.

When P1 becomes greater than 150 mm Hg 304, an alarm will sound 306 (FIG. 8) notifying the operator of the condition. The control unit CU initially attempts to lower P1 by decreasing the blood pump speed gradually. Therefore, as long as the blood pump speed remains above an average flow rate of 250 ml/min. 307, the blood pump speed will gradually be decreased 308 in an attempt to lower the P1 value. When, after gradually decreasing the blood pump speed, it becomes necessary to reduce the blood flow rate (i.e., pump speed) below 250 ml/min. 309 in an effort to keep P1 below 150 mm Hg, the control unit CU determines if the blood pump 52 is still operating at a rate greater than a minimum level below which blood purification and reinfusion cannot take place (e.g., 100 ml/min) 310. If the blood pump speed is still greater than the minimum speed 311, the control unit CU stops membrane filtration and goes into reverse filtration mode 312 for a pre-set period of time, t. The membrane should be cleared of clots and debris during the reverse filtration process. Following the time period for reverse filtration (i.e., t+δt), membrane filtration is re-commenced by the control unit CU, 300. If, upon measurement 302, P1 is still greater than 150 mm Hg 304, the blood pump speed is less than 250 ml/min. 309, and is even less than the minimum speed for purification and blood reinfusion (100 ml/min.) 316, the operator is called for assistance 318. The operator may then check for any blockage in the reinfusion line 98, the venous catheter 100, the venous valve 97 and/or the venous filter 94.

Figure 4:
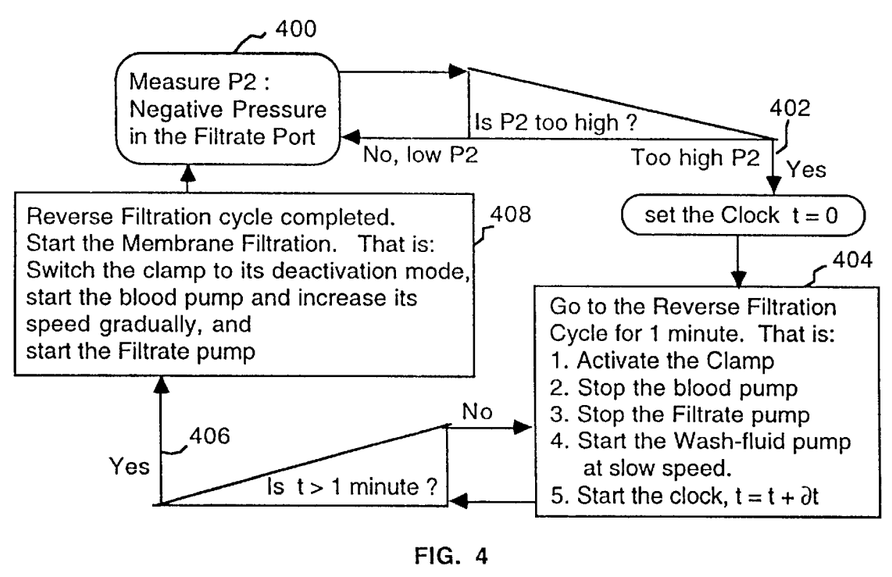
FIG. 4 is a schematic diagram illustrating the function and control logic of the negative pressure sensor (P2) located at the membrane filter filtrate outlet.

FIG. 4 schematically illustrates the control logic and interaction of the negative pressure sensor 64 with the clamp 50, the washing fluid pump 38, the blood pump 52 and the filtrate pump 76. A maximum limit for the negative pressures which may be sustained on the filtrate side 61 of the membrane filter 54 is set by the filter manufacturers and is determined by the degree of damage to which the blood cells and membrane filter may be subjected at high negative pressures. The maximum safe negative pressure of a membrane filter varies with the membrane characteristics and method of assembly of each kind and make of membrane filter. Normally, membrane filtration proceeds within the safe limits of negative pressure P2 on the filtrate side 61. However, with continuous blood filtration over a long period of time, the membrane pores may become clogged with protein and cellular deposits. In time, such deposits may grow to form a gel on the membrane surface, which, in turn, may impose additional resistance to proper filtration. This gel formation may increase the negative pressure necessary to obtain the desired filtration rate.

Negative pressure P2 is measured at the filtrate port 72 by pressure sensor 64, as indicated in FIG. 4 at 400. When the negative pressure increases beyond the selected safe limit 402, the system automatically switches from filtration to reverse filtration 404 for a pre-set period of time, t. At that time, the clamp 50 is activated, thereby closing off the blood line 96 and washing fluid line 48, the blood pump 52 and filtrate pump 76 stop and the washing fluid pump 38 is operated at a slow speed. FIG. 4 suggests that the period of reverse filtration may be one minute; however, the time period may be selected to any desired value by the operator. At the end of the period of reverse filtration 406 (i.e., t+67 t), the system returns to membrane filtration 408 automatically. At that time, the clamp 50 is deactivated, thereby opening blood line 96 and washing fluid line 48, the speed of the blood pump 52 gradually increases, and the filtrate pump 76 begins to operate.

Figure 5:
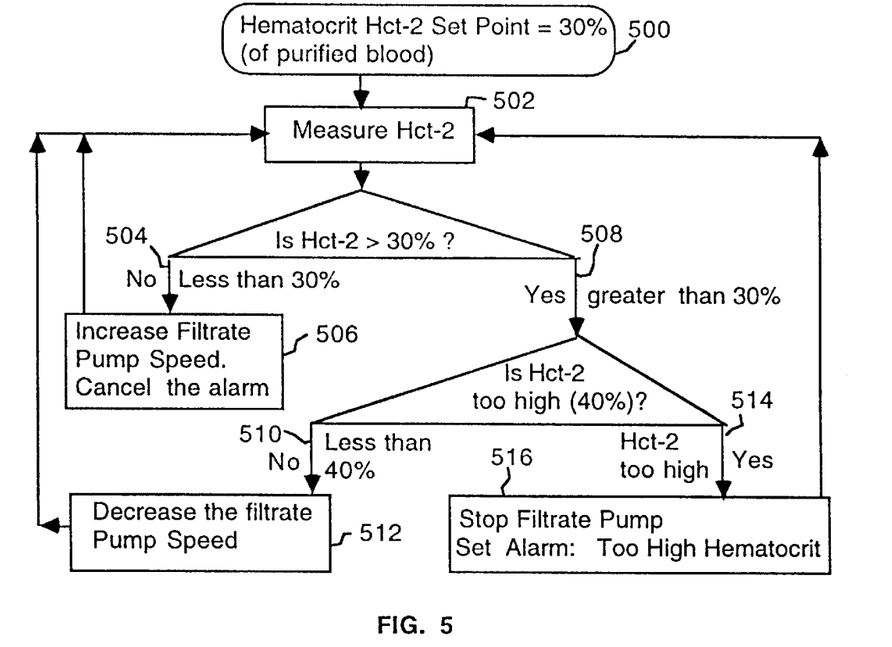
FIG. 5 is a schematic diagram illustrating the function and control logic of the hematocrit sensor (HCT-2) located at the blood exit port of the membrane filter.

FIG. 5 shows the operating logic of the hematocrit HCT-2 sensor 88 located at the blood exit port 90 of the membrane filter 54, and its interaction with the filtrate pump 76. The hematocrit HCT-2 of the washed and filtered blood that is to be reinfused to the patient is controlled at a selected value by regulating the filtration rate through the membrane filter 54. The desired value of the hematocrit HCT-2 may be selected by the operator 500, and is shown in FIG. 5, for example, to be 30%. The hematocrit HCT-2 level is constantly measured 502. When the measured HCT-2 value drops below the selected value 504, the filtration rate is increased automatically by increasing the filtrate pump speed 506. When the HCT-2 value rises above the selected limit 508, but is less than a selected upper limit (e.g., 40%) 510, the filtrate pump speed is decreased 512 to bring the HCT-2 value back into range. However, when the HCT-2 value exceeds the upper limit, (e.g., above 40%) 514, then the filtrate pump is stopped 516 until such time as the HCT-2 value is near 30%. It may be noted that an HCT-2 value above 50% may cause hemolysis in the membrane filter 54 and may lead to excessive pressure at P1. It may be appreciated that for the above reasons, the blood salvaging system of the present invention automatically acts to prevent excessive HCT-2 values at the blood exit port 90.

Figure 6:
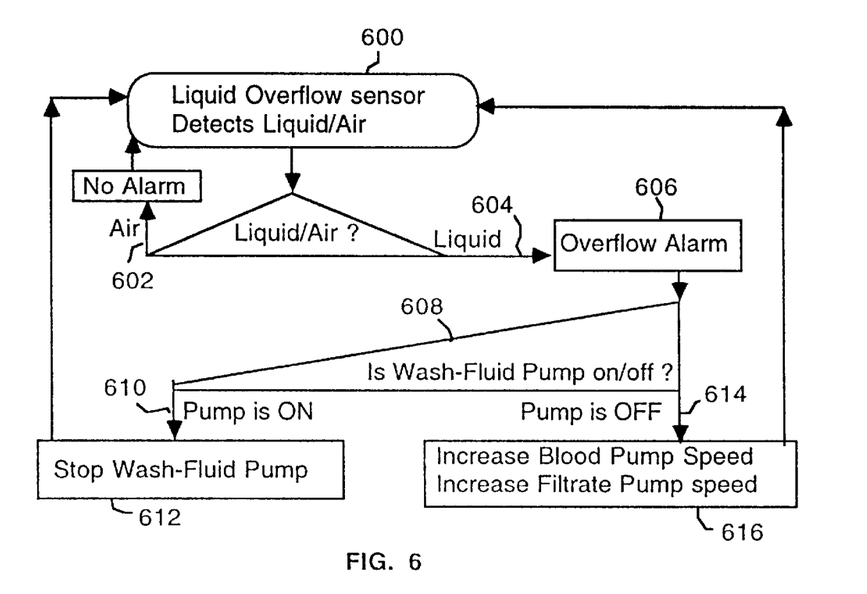
FIG. 6 is a schematic diagram illustrating the function and control logic of the overflow sensor located at the top end of the cardiotomy reservoir.

FIG. 6 describes the operating logic of the overflow liquid sensor 34 and its interaction with the washing fluid pump 38, the blood pump 52 and the filtrate pump 76. Liquid in the reservoir 20 may overflow due to the addition of too much washing fluid by the washing fluid pump and/or due to high amounts of blood being aspirated as a result of excessive bleeding in the wound site. The overflow of liquid in the reservoir 20 is sensed by an air-liquid sensor 34, which may be an ultrasonic sensor or photoelectric sensor. However, in the present invention, a hematocrit sensor 34 connected to the wall of the reservoir 20 near the top end thereof is used to detect the air-liquid interface, indicated at 600 in FIG. 6. Under normal conditions, when the overflow sensor detects air 602, the resulting measured hematocrit value becomes a negative value. However, when the sensor 34 detects liquid 604, it measures either a zero or a positive value. An overflow alarm is activated 606 and the control unit CU determines if the washing fluid pump is on or off 608. If the washing fluid pump is on 610, it is stopped 612 to prevent any further dilution of the aspirated blood in the reservoir 20. If the control unit CU determines that the washing fluid pump is already off 614, the speed of the blood pump and the speed of the filtrate pump is increased 616 to the maximum pre-set limit in an effort to remove liquid from the reservoir 20 and thereby eliminate the overflow condition quickly.

Figure 7:
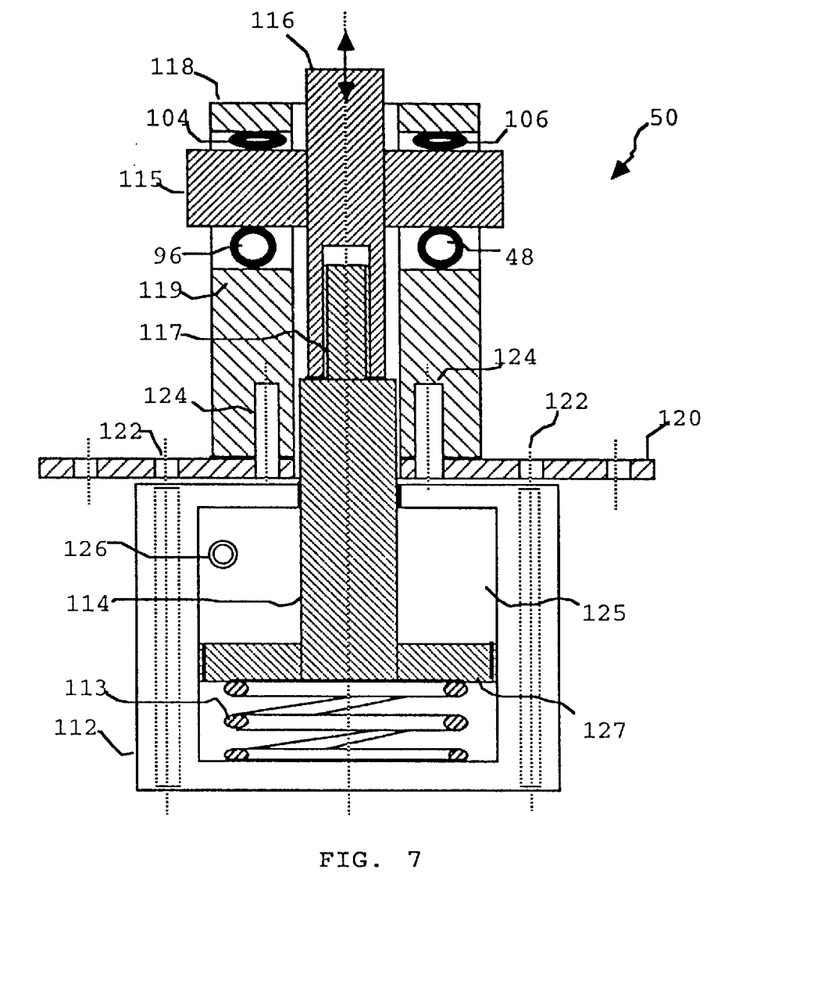
FIG. 7 is a representational cross section view of the pneumatically driven tubing clamp.

FIG. 7 illustrates the pneumatically driven, multichannel clamp 50 used in the present invention. Any pneumatic piston may be used in the invention, but a piston commercially known as a pancake piston may be particularly suitable. The pancake piston, illustrated in FIG. 7, comprises a pneumatic piston 112, a piston shaft 114, a piston shaft rod 116 connected to the piston shaft 114, an occluder 115 attached to the piston shaft rod 116, an upper tubing guide 118 positioned parallel to the occluder 115 and a lower tubing guide 119 positioned parallel to the occluder 115. The clamp 50 is structured to retain two tubes, namely blood line 104 and washing fluid line 106, between the upper tubing guide 118 and the occluder 115, and two tubes, namely blood line 96 and washing fluid line 48 between the occluder 115 and the lower tubing guide 119. The piston 112 is attached to a flange 120 by means of two threaded bolts 122. The upper tubing guide 118 and lower tubing guide 119 are also attached to the flange 120 by means of two threaded bolts 124. The piston shaft rod 116 is attached coaxially to the piston shaft 114 through a threaded pin 117. The occluder 115 is attached to the piston shaft rod 116, in perpendicular orientation thereto, and is movable therewith as the piston shaft rod 116 moves up and down with the piston shaft 114.

The piston 112 includes an internal chamber 125 having a port 126 through which high pressure air is applied to the chamber 125. A barrier 127, slidably positioned within the chamber 125, is attached to the piston shaft 114 and is movable with the piston shaft 114. A tension spring 113 is biased between the barrier 127 and the bottom of the chamber 125 and forces the barrier 127, and thus the piston shaft 114, upwardly under normal conditions (i.e., when high pressure air is not supplied to the chamber 125). The clamp 50 is, therefore, in a deactivated mode. The upward force of the tension spring 113 on the piston shaft 114 and piston shaft rod 116 also forces the occluder 115 against the upper tubing guide 118 to compress tubing lines 104 and 106 positioned therebetween. The occluder 115 is spaced from the lower tubing guide 119 and, as a result, the tubing lines 48 and 96 remain open during deactivation of the clamp 50.

When the clamp 50 is activated by the application of approximately 1500 mm Hg air pressure through the port 126, the barrier 127 is forced downward, thereby forcing the tension spring 113 down as well. As the tension spring 113 is compressed by the application of high pressure air to the chamber 125, the piston shaft 114 is forced downward, as are the piston shaft rod 116 and occluder 115. As the occluder 115 moves downward and away from the upper tubing guide 118, compression of tubing lines 104 and 106 is released, thereby opening those lines. Simultaneously, as the occluder 115 approaches the lower tubing guide 119, tubing lines 48 and 96 become compressed therebetween and are closed off. When the clamp 50 is in the activated mode as just described, the blood salvaging apparatus is in the reverse filtration mode. It may be noted that instead of employing a pneumatic system for the clamp 50, a vacuum system may be used to effect alternating compression of the tubing lines.

However, the vacuum may not provide adequate force required to occlude the tubings completely, especially when the fluid pressures in the tubings are high. In the present invention, the reliability and simplicity of the system is improved by the use of the above-described single clamp 50, instead of two or more clamps to switch from membrane filtration to reverse filtration.

FIG. 8 illustrates the relationship between the blood salvaging elements of the invention and the control unit CU. The structural components of the blood salvaging apparatus shown in FIG. 8 are the same as those shown in FIG. 1A, except that these components are shown to be mounted on an instrument cabinet 800 consisting of a control unit CU front panel and an i.v. pole 802, but the individual elements are not shown to scale or in correct size relative to each other. The control unit front panel shows knobs for setting standby time STANDBY T 804 (e.g., one minute), reverse filtration time RF TIME 806 (e.g., one minute), maximum positive pressure P1 MAX 808 (e.g., 150 mm Hg), and maximum negative pressure P2 MAX 810 (e.g., −50 mm Hg).

The control unit front panel also shows four dual set point relay meters which continuously display hematocrit values HCT-1 812 and HCT-2 814, blood pump speed 816 and washing fluid pump speed 818. Also, maximum and minimum set point values can be set on these dual set point relay meters by the operator for HCT-1 (e.g., 0% to 11.7%), HCT-2 (e.g., 30% to 40%), blood pump speed (e.g., 100 ml/min to 500 ml/min), and washing fluid pump speed (e.g., 100 ml/min to 500 ml/min.). Such dual set point relay meters are commercially available from, for example, API Instruments, Chesterland, Ohio.

Also shown in FIG. 8 are alarm indicators, both audio and visual, for indicating high positive pressure P1 in the blood inlet port 58, high negative pressure P2 in the filtrate port 72, high hematocrit HCT-2 at the blood exit port 90, the presence of air in the venous filter 94, overflow in the cardiotomy reservoir 20, and visual indicators for different modes of operation (i.e., filtration mode, standby mode, and reverse filtration mode). The control unit displays and meters can be configured in many different ways by those skilled in the electrical arts.

The autologous blood salvaging system of the present invention provides distinct advantageous over prior blood recovery systems. The blood salvaging system of the present invention may be used for humans as well as animals, with some minor variations. Thus, reference herein to specific details of the illustrated embodiments is by way of example and not by way of limitation. It will be apparent to those skilled in the art that many modifications of the basic illustrated embodiment may be made without departing from the spirit and scope of the invention as recited by the claims.

What is claimed is:

1. An autologous blood salvaging apparatus comprising:
a suction device for aspirating blood from a wound or surgical site;
an emboli filter in fluid communication with said suction device for receiving and filtering said aspirated blood therethrough;
a reservoir connected to said emboli filter for temporarily retaining blood;
a source of washing fluid in fluid communication with said emboli filter for admixing washing fluid with said aspirated blood prior to entry into said emboli filter;
a washing fluid pump positioned relative to said source of washing fluid to move washing fluid from said source of washing fluid to admix with said aspirated blood;

a hematocrit sensor attached to said reservoir for detecting the hematocrit level of said blood, said sensor being in electrical communication with said washing fluid pump to regulate the speed of said washing fluid pump responsive to a detected hematocrit level in the aspirated blood;

a membrane filter in fluid communication with said emboli filter for receiving and purifying washed blood from said reservoir; and a reinfusion conduit in fluid communication with said membrane filter for delivering washed and purified blood for reinfusion to a patient.

2. The autologous blood salvaging apparatus of claim 1 further comprising a blood pump in fluid communication with said reservoir and said membrane filter, and being in electrical communication with said hematocrit sensor.

3. The autologous blood salvaging apparatus of claim 2 further comprising a filtrate means attached to said membrane filter for removing filtered waste and fluid separated from said blood passing through said membrane filter.

4. The autologous blood salvaging apparatus of claim 3 further comprising a filtrate pump in fluid communication with said filtrate means for urging removal of filtrate from said membrane filter, said filtrate pump being in electrical communication with said hematocrit sensor.

5. The autologous blood salvaging apparatus of claim 4 further comprising a blood collection bag in fluid communication with said membrane filter for receiving washed and filtered blood from said membrane filter, an emboli detector positioned downstream from said blood collection bag and a clamp positioned downstream from said emboli detector and in electrical communication therewith to prevent blood from being reinfused responsive to the detection of emboli in the blood.

6. The autologous blood salvaging apparatus of claim 5 further comprising an overflow sensor connected to said reservoir and positioned to detect the level of liquid in said reservoir, said overflow sensor being in electrical communication with said blood pump, said filtrate pump and said washing fluid pump.

7. The autologous blood salvaging apparatus of claim 4 wherein said source of washing fluid further comprises a first washing fluid conduit extending between said source of washing fluid and said suction device, and a second washing fluid conduit extending between said source of washing fluid and said membrane filter, and wherein said apparatus further comprises a first blood conduit extending from the outlet of said membrane filter to said reinfusion conduit and a second blood conduit extending from said outlet of said membrane filter to said emboli filter.

8. The autologous blood salvaging apparatus of claim 7 further comprising a clamp for engaging said first washing fluid conduit, said second washing fluid conduit, said first blood conduit and said second blood conduit and alternately clamping said second washing fluid conduit and second blood conduit while leaving unclamped said first washing fluid conduit and second blood conduit, said clamp being in electrical communication with said hematocrit sensor, said blood pump, said washing fluid pump and said filtrate pump.

9. The autologous blood salvaging apparatus of claim 8 further comprising a positive pressure sensor positioned in proximity to the inlet of said membrane filter for detecting positive pressure of blood entering into said membrane filter, said positive pressure sensor being in electrical communication with said washing fluid pump, said filtrate pump, said blood pump and said clamp.

10. The autologous blood salvaging apparatus of claim 9 further comprising a negative pressure sensor connected to the filtrate side of said membrane filter for detecting negative pressure conditions therein, said negative pressure sensor being in electrical communication with said washing fluid pump, said filtrate pump, said blood pump and said clamp.

11. The autologous blood salvaging apparatus of claim 10 further comprising a second hematocrit sensor positioned in proximity to said outlet of said membrane filter for detecting the hematocrit in reinfusable blood, said second hematocrit sensor being in electrical communication with said filtrate pump.

12. The autologous blood salvaging apparatus of claim 11 further comprising an overflow sensor connected to said reservoir and positioned to detect a maximum level of liquid in said reservoir, said overflow sensor being in electrical communication with said washing fluid pump, said blood pump and said filtrate pump.

13. The autologous blood salvaging apparatus of claim 12 further comprising a programmable control unit to which said hematocrit sensor, said blood pump, said filtrate pump, said washing fluid pump, said clamp, said positive pressure sensor, said negative pressure sensor, said overflow sensor and said second hematocrit sensor are in electrical communication.

14. The autologous blood salvaging apparatus of claim 1 further comprising reverse filtration apparatus connected to said membrane filter for flushing accumulated matter from the membrane of said membrane filter.

15. The autologous blood salvaging apparatus of claim 14 further comprising filtrate means connected to said membrane filter for removing filtrate fluid separated from blood.

16. A method of filtering and reinfusing autologous blood removed from a patient comprising:

aspirating blood from a wound or surgical site;

diluting said aspirated blood with a washing fluid in a proportion responsive to a detected hematocrit level in an admixture of accumulated aspirated blood and washing fluid in a blood reservoir;

filtering said diluted blood through an emboli filter associated with said blood reservoir;

filtering said diluted blood from said emboli filter and blood reservoir through a membrane filter comprising a porous membrane to remove from said diluted blood fluid and particulate matter sized above a selected molecular size;

removing filtrate fluid from said membrane filter which is separated from filtered blood;

monitoring filtered blood exiting from said membrane filter to detect the presence of emboli therein; and reinfusing emboli-free blood to said patient.

17. The method according to claim 16 further comprising conducting reverse filtration of said membrane filter by directing washing fluid through said porous membrane in a direction opposite the filtration of blood.

18. The method according to claim 17 wherein said reverse filtration is conducted responsive to the detection of air in said reservoir corresponding to a low level of liquid in said reservoir.

19. The method according to claim 17 further comprising monitoring the level of positive pressure existing in the blood immediately prior to filtering through said membrane filter.

20. The method according to claim 19 comprising conducting reverse filtration responsive to a detected level of positive pressure in said blood above a selected level.

21. The method according to claim 19 further comprising monitoring the level of negative pressure existing on the filtrate side of said membrane filter.

22. The method according to claim 21 comprising conducting reverse filtration responsive to a detected level of negative pressure existing on the filtrate side of the membrane filter above a selected negative pressure value.

23. The method according to claim 21 further comprising monitoring the hematocrit level of blood exiting from said membrane filter to maintain a selected hematocrit level in the blood for reinfusion and selectively modifying the rate of removal of filtrate from said membrane filter responsive to the detected hematocrit level in the blood exiting the membrane filter.

24. The method according to claim 23 further comprising detecting the level of liquid in said reservoir associated with the emboli filter and selectively increasing the flow rate of blood through said membrane filter responsive thereto.

25. The method according to claim 17 further comprising monitoring the level of negative pressure existing on the filtrate side of said membrane filter.

26. The method according to claim 25 comprising conducting reverse filtration responsive to a detected level of negative pressure existing on the filtrate side of the membrane filter above a selected negative pressure value.

27. The method according to claim 16 further comprising monitoring the hematocrit level of blood exiting from said membrane filter to maintain a selected hematocrit level in the blood for reinfusion.

28. The method according to claim 27 further comprising selectively modifying the rate of removal of filtrate from said membrane filter responsive to the detected hematocrit level in the blood exiting the membrane filter.

29. The method according to claim 16 further comprising detecting the level of liquid in said reservoir associated with the emboli filter and selectively modifying the rate at which washing fluid is introduced into said reservoir responsive thereto.

* * * * *